United States Patent
Lin et al.

(10) Patent No.: US 9,475,016 B2
(45) Date of Patent: Oct. 25, 2016

(54) FLUID MIXING STRUCTURE

(71) Applicant: HTC Corporation, Taoyuan (TW)

(72) Inventors: Sheng-Chieh Lin, Taoyuan (TW);
Pin-Chung Sun, Taoyuan (TW);
Yao-Ting Tseng, Taoyuan (TW);
Shih-Jen Lu, Taoyuan (TW);
Chung-Ju Wu, Taoyuan (TW);
Chien-Lung Huang, Taoyuan (TW)

(73) Assignee: HTC Corporation, Taoyuan (TW)

( * ) Notice: Subject to any disclaimer, the term of this patent is extended or adjusted under 35 U.S.C. 154(b) by 63 days.

(21) Appl. No.: 14/555,689

(22) Filed: Nov. 28, 2014

(65) Prior Publication Data
US 2016/0151750 A1 Jun. 2, 2016

(51) Int. Cl.
*B01F 3/08* (2006.01)
*B01F 5/06* (2006.01)
*G01N 1/38* (2006.01)

(52) U.S. Cl.
CPC ............ *B01F 3/0861* (2013.01); *B01F 5/061* (2013.01); *G01N 1/38* (2013.01); *B01F 2005/0631* (2013.01); *B01F 2005/0636* (2013.01); *B01F 2215/0037* (2013.01)

(58) Field of Classification Search
CPC ............ B01F 13/0064; B01F 13/0861; B01F 3/0861
USPC .......................................... 366/337, 340–341
See application file for complete search history.

(56) References Cited

U.S. PATENT DOCUMENTS 3,361,413 A * 1/1968 Heyl .................. B01F 5/243
366/137
3,860,129 A * 1/1975 Bieth .................. B65G 69/10
222/459

(Continued)

FOREIGN PATENT DOCUMENTS

CN  201551969  8/2010
JP  H02144136  6/1990

(Continued)

OTHER PUBLICATIONS

"Office Action of Taiwan Counterpart Application", issued on Mar. 22, 2016, p. 1-4.

*Primary Examiner* — Walter D Griffin
*Assistant Examiner* — Abbas Rashid
(74) *Attorney, Agent, or Firm* — Jianq Chyun IP Office

(57) ABSTRACT

A fluid mixing structure adapted to mix a reagent liquid and a sample liquid is provided. The fluid mixing structure includes a first channel, a mixing recess, a first block, a plurality of second blocks, and a second channel. The mixing recess is communicated with the first channel. The first block is disposed in the mixing recess, so that the mixing recess becomes a ring-shaped channel. The second blocks are disposed in the ring-shaped channel. The reagent liquid and the sample liquid are mixed into a mixing liquid in the ring-shaped channel. The second channel is communicated with the mixing recess. The mixing liquid flows out of the mixing recess through the second channel.

6 Claims, 2 Drawing Sheets

(56) References Cited

U.S. PATENT DOCUMENTS

| | | | | |
|---|---|---|---|---|
| 4,285,602 A * | 8/1981 | Hagerty | ............... | B01F 5/242 366/101 |
| 4,518,260 A * | 5/1985 | Goins | ............... | B01F 5/242 366/134 |
| 4,724,754 A * | 2/1988 | Crozat | ............... | A23G 3/0215 165/145 |
| 2003/0235111 A1* | 12/2003 | Bishop | ............... | B01F 5/243 366/341 |
| 2009/0251989 A1* | 10/2009 | Pfefferle | ............... | B01F 5/0453 366/340 |
| 2010/0103769 A1* | 4/2010 | Bachman | ............... | B01F 3/0446 366/340 |
| 2012/0014209 A1* | 1/2012 | Smith | ............... | B01F 5/0451 366/340 |
| 2012/0300577 A1* | 11/2012 | Buttridge | ............... | B01J 8/0492 366/340 |
| 2013/0215705 A1* | 8/2013 | Mueller | ............... | A61C 3/025 366/165.2 |
| 2014/0038209 A1 | 2/2014 | Shih et al. | | |

FOREIGN PATENT DOCUMENTS

| | | |
|---|---|---|
| JP | H08332364 | 12/1996 |
| TW | 429288 | 4/2001 |

* cited by examiner

FLUID MIXING STRUCTURE

FIELD OF THE PRESENT INVENTION

The present application relates to a fluid mixing structure; and more particularly, to a fluid mixing structure for mixing liquids.

DESCRIPTION OF RELATED ART

In recent years, miniaturized biochemical analysis systems have been developed. Many miniaturized inspection devices have also been applied in various kinds of analysis systems. Advantages of miniaturizing biochemical analysis systems include fast analyses, accurate quantification, low amount requirement of sample and space-saving, and the like. Therefore, many inspection devices have been developed to become miniaturized, or are even integrated to a single module.

In the existing biochemical analysis systems, a sample liquid and a reagent liquid may be mixed in a micro-channel structure, and then flow through a biochip, such that a biological property thereof is inspected. The micro-channel structure may be designed based on needs, such that the sample liquid with slight volume and the reagent liquid are mixed or separate out partial ingredients thereof when passing through the micro-channel structure. However, when the sample liquid and the reagent liquid have low Reynolds numbers, it is difficult for the sample liquid and the reagent liquid to be mixed evenly during flowing in the micro-channel due to a limited size of the micro-channel. Such situation causes inaccurate inspection results which are obtained by the biochip which subsequently inspects the mixing liquid.

SUMMARY OF THE PRESENT INVENTION

The present application provides a fluid mixing structure, which is adapted to mix a reagent liquid and a sample liquid evenly.

A fluid mixing structure of the present application is adapted to mix a reagent liquid and a sample liquid. The fluid mixing structure includes a first channel, a mixing recess, a first block, a plurality of second blocks, and a second channel. The mixing recess is communicated with the first channel. The reagent liquid and the sample liquid flow into the mixing recess through the first channel. The first block is disposed in the mixing recess, so that the mixing recess becomes a ring-shaped channel by the first block. The second blocks are disposed in the ring-shaped channel. The reagent liquid and the sample liquid are mixed into a mixing liquid in the ring-shaped channel. The second channel is communicated with the mixing recess. The mixing liquid flows out of the mixing recess through the second channel.

In view of the above, in the fluid mixing structure of the present application, the first channel, the mixing recess, and the second channel are communicated with each other, wherein the first block is disposed in the mixing recess, such that the mixing recess becomes a ring-shaped channel through the first block, and the second blocks are disposed in the ring-shaped channel. Accordingly, the reagent liquid and the sample liquid flow into the mixing recess through the first channel, and are mixed into the mixing liquid in the mixing recess, and then flow out of the mixing recess through the second channel. Accordingly, the reagent liquid and the sample liquid are disturbed by the second blocks in the ring-shaped channel, so that mixing evenness is increased. Therefore, the fluid mixing structure of the present application is adapted to mix the reagent liquid and the sample liquid evenly.

Several exemplary embodiments accompanied with figures are described in detail below to further describe the present application in details.

BRIEF DESCRIPTION OF THE DRAWINGS

The accompanying drawings are included to provide a further understanding of the present application, and are incorporated in and constitute a part of this specification. The drawings illustrate embodiments of the present application and, together with the description, serve to explain the principles of the present application.

DETAILED DESCRIPTION OF DISCLOSED EMBODIMENTS

Figure 1:
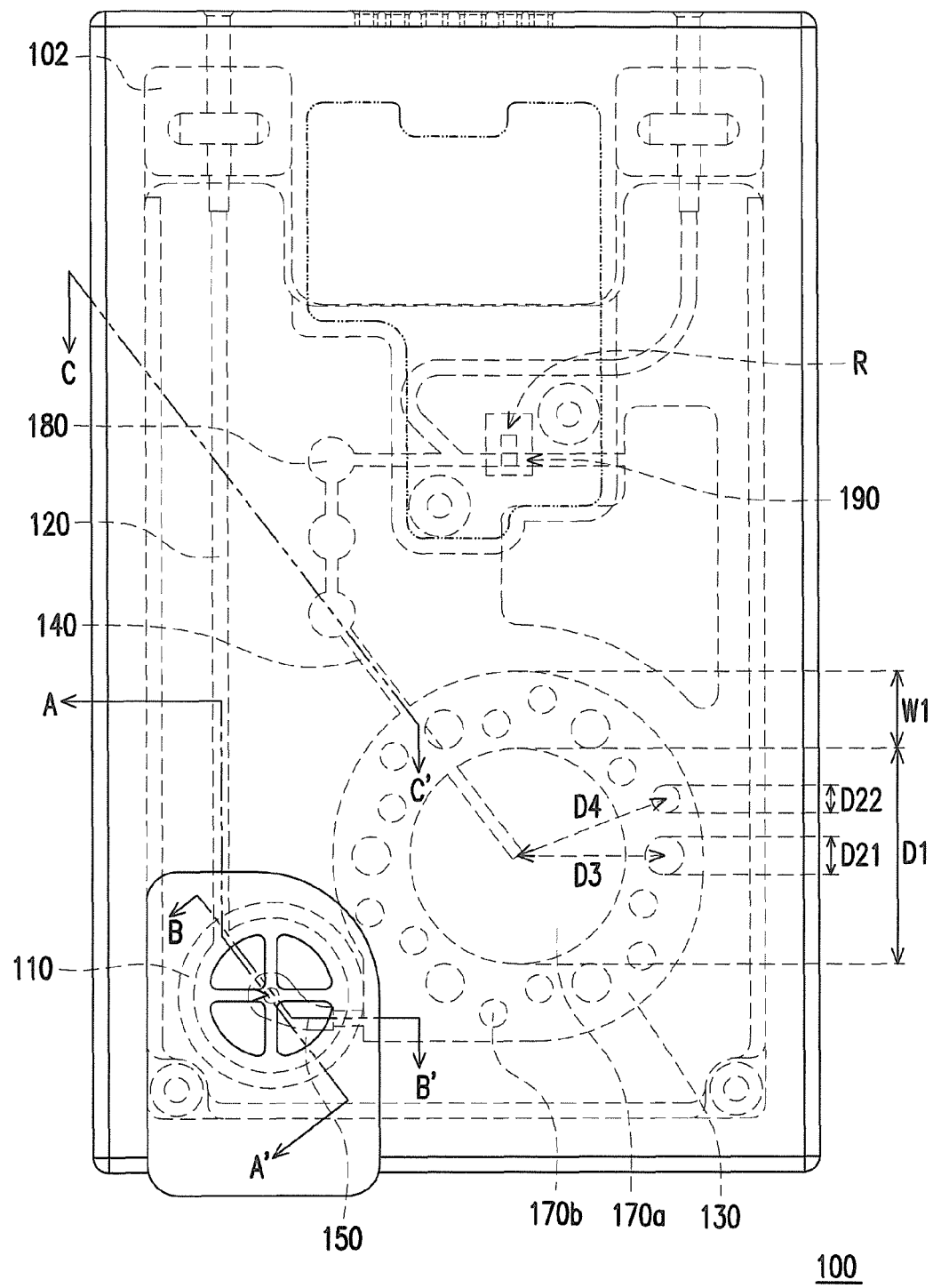
FIG. 1 is a schematic top view illustrating a fluid mixing structure according to an embodiment of the present invention.

Reference will now be made in detail to the present preferred embodiments of the present application, examples of which are illustrated in the accompanying drawings. Wherever possible, the same reference numbers are used in the drawings and the description to refer to the same or like parts.

Figure 2:
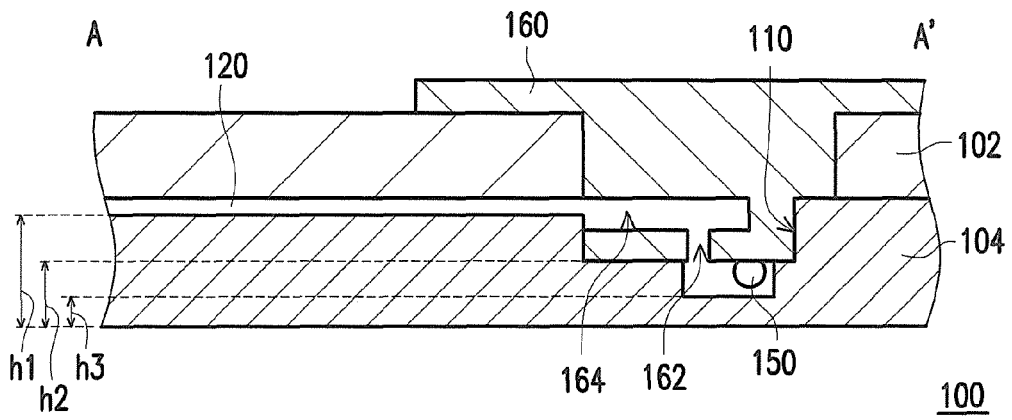
FIG. 2 is a schematic cross-sectional view illustrating the fluid mixing structure depicted in FIG. 1 along line A-A'.

FIG. 1 is a schematic top view illustrating a fluid mixing structure according to an embodiment of the present invention. FIG. 2 is a schematic cross-sectional view illustrating the fluid mixing structure depicted in FIG. 1 along line A-A'. With reference to FIG. 1 and FIG. 2, in the present embodiment, a fluid mixing structure 100 includes an accommodating recess 110, a third channel 120, a mixing recess 130, and a second channel 140, wherein the third channel 120 is communicated with the accommodating recess 110, the mixing recess 130 is communicated with the accommodating recess 110, and the second channel 140 is communicated with the mixing recess 130. The fluid mixing structure 100 of the present embodiment may be fabricated by adopting two plates 102 and 104. In addition, the accommodating recess 110, the third channel 120, the mixing recess 130, and the second channel 140 are recesses or trenches which are disposed on either the plate 102 or the plate 104, and located between the plates 102 and 104 after the plates 102 and 104 are bonded by adopting a double-sided adhesive tape or other suitable manners. Furthermore, after the plates 102 and 104 are fabricated, they may be disposed in a housing, such that the fluid mixing structure 100 is deemed as one part of an inspecting module. Accordingly, in FIG. 1, the plates 102 and 104, and structures which are located between the plates 102 and 104 (e.g., the accommodating recess 110, the third channel 120, the mixing recess 130, and the second channel 140) are illustrated in dashed line. Moreover, the fluid mixing structure 100 further includes a first channel 150. The first channel 150 is communicated with the accommodating recess 110, and the mixing recess 130 is communicated with the first fluid 150. Accordingly, the accommodating recess 110 is adapted to accommodate a sample liquid which is not illustrated herein, and a reagent liquid which is not illustrated herein is adapted to flow into the accommodating recess 110 through the third channel 120. Afterwards, the reagent liquid entrains the sample liquid in the accommodating recess 110. Then, the reagent liquid and the sample liquid flow into the mixing recess 130 through the first channel 150, and are further mixed into a mixing liquid in the mixing recess 130. In other words, two different liquids (the reagent liquid and the sample liquid) may be mixed in the mixing recess 130. In addition, the mixing liquid which is a mixture of the reagent liquid and the sample liquid in the mixing recess 130 may flow out of the mixing recess 130 through the second channel 140. The detailed description is given as follows.

Specifically, in the present embodiment, the inspecting module further includes a liquid collector 160 which is disposed in the accommodating recess 110. In other words, the accommodating recess 110 may be deemed as a recess structure which is located on the plates 102 and 104 and communicated with an exterior, while the liquid collector 160 is adapted to collect the sample liquid and be assembled in the accommodating recess 110 after collecting sample liquid. Thus, after the reagent liquid flows into the accommodating recess 110 through the third channel 120, the reagent liquid flows into the liquid collector 160 which is disposed on the accommodating recess 110, and then entrains the sample liquid in the liquid collector 160, so as to flow into the mixing recess 130 through the first channel 150 thereafter. To be more specific, the liquid collector 160 has a through hole 162 and a passage 164 which are communicated with each other. When the liquid collector 160 is disposed in the accommodating recess 110, the passage 164 and the through hole 162 are communicated with the third channel 120 and the first channel 150, respectively. Accordingly, the third channel 120, the passage 164, the through hole 162, the first channel 150, and the mixing recess 130 form a continuous flowing path. The reagent liquid and the sample liquid are arranged at different locations of the flowing path, respectively. For example, an initial location of the reagent liquid is at the third channel 120, and an initial location of the sample liquid is at the through hole 162. Accordingly, the reagent liquid may flows from the third channel 120 into the passage 164 of the liquid collector 160 (which is located in the accommodating recess 110). Then, after the reagent liquid entrains the sample liquid in the through hole 162, the reagent liquid and the sample liquid flow into the mixing recess 130 through the first channel 150. However, the liquid collector 160 is only an implementation of the present application which is configured for collecting the sample liquid. For example, the sample liquid may also be dripped directly into the accommodating recess 110, or be placed in the accommodating recess 110 after being loaded in other containers. The present application does not limit ways of arranging the sample liquid.

Figure 3:
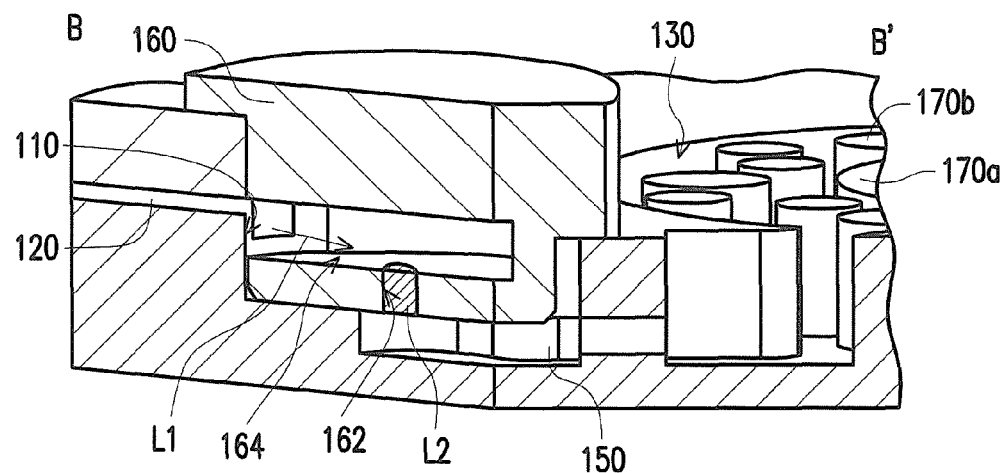
FIG. 3 is a partial cross-sectional view illustrating the fluid mixing structure depicted in FIG. 1 along line B-B'.

FIG. 3 is a partial cross-sectional view illustrating the fluid mixing structure depicted in FIG. 1 along line B-B'. With reference to FIG. 1 to FIG. 3, in the present embodiment, the fluid mixing structure 100 further includes a first block 170a. The first block 170a is disposed in the mixing recess 130, so that the mixing recess 130 becomes a ring-shaped channel by the first block 170a. Specifically speaking, the mixing recess 130 is substantially a circle, and a volume thereof is preferably bigger than volumes of the accommodating recess 110, the third channel 120, the second channel 140, and the first channel 150. In addition, the first block 170a is a cylinder, and is preferably disposed in a middle portion of the mixing recess 130, so that the other portion of the mixing recess 130 which is not occupied by the first block 170a becomes a ring-shaped channel. Accordingly, the mixing recess 130 may be configured for mixing the reagent liquid and the sample liquid which flow in from the accommodating recess 110 through the first channel 150, and the ring-shaped channel formed in the mixing recess 130 by the first block 170a facilitates mixing of the reagent liquid and the sample liquid. More specifically, when a reagent liquid L1 (shown as an arrow in FIG. 3) entrains a sample liquid L2 (shown as oblique lines filled in the through hole 162 in FIG. 3) in the liquid collector 160, the sample liquid L2 is entrained by the reagent liquid L1 and flows, together with the reagent liquid L1, out of the liquid collector 160, and then flow into the mixing recess 130 through the first channel 150. In other words, before the reagent liquid L1 and the sample liquid L2 flow into the mixing recess 130, both liquids are not completely mixed. Since the mixing recess 130 has larger volume and the mixing recess 130 becomes the ring-shaped channel by the first block 170a (as shown in FIG. 1), after the reagent liquid L1 and the sample liquid L2 flow together into the mixing recess 130, the reagent liquid L1 and the sample liquid L2 may mix with each other when flowing in the ring-shaped channel formed in the mixing recess 130.

In addition, in the present embodiment, the fluid mixing structure 100 further includes a plurality of second blocks 170b. The second blocks 170b are disposed in the ring-shaped channel of the mixing recess 130. The reagent liquid L1 and the sample liquid L2 are mixed into a mixing liquid in the ring-shaped channel of the mixing recess 130 by the second blocks 170b. In other words, the fluid mixing structure 100 of the present embodiment is provided with not only the first block 170a to form the ring-shaped channel in the mixing recess 130, but also the second block 170b to increases mixing effects, wherein, the second blocks 170b are distributed in the ring-shaped channel, and sizes of the second blocks 170b are inconsistent. For example, the second blocks 170b may be cylinders, but the present application does not limit shapes of the second blocks 170b. Herein, a diameter D1 of the first block 170a is greater than diameters D21 and D22 of the second blocks 170b. Thus, the first block 170a is configured for forming the ring-shaped channel, while the second blocks 170b is configured for forming a turbulence structure in the ring-shaped channel, such that the reagent liquid L1 and the sample liquid L2 which flow into the ring-shaped channel are disturbed by the second blocks 170b and mixed evenly. Preferably, the diameters D21 and D22 of the second blocks 170b are inconsistent. In addition, distances D3 and D4 from centers of the second blocks 170b to a center of the first block 170a are inconsistent. Namely, locations of the second blocks 170b relative to the first block 170a are inconsistent. Furthermore, in the present embodiment, a width W1 of the ring-shaped channel ranges between twice and triple the diameters D21 and D22 of the second blocks 170b, which means that, with respect to the ring-shaped channel, the sizes of the second blocks 170b are smaller, so as to be deemed as the turbulence structure, and distribution density of the second blocks 170b in the ring-shaped channel may be adjusted as desired.

Accordingly, after the reagent liquid L1 and the sample liquid L2 flow into the mixing recess 130, the reagent liquid L1 and the sample liquid L2 flow in the ring-shaped channel which is formed in the mixing recess 130, and generate vortex due to turbulence of the second blocks 170b which are arranged in an asymmetric manner. In other words, the reagent liquid L1 and the sample liquid L2, after converging in the liquid collector 160 of the accommodating recess 110, flow into the mixing recess 130, and mix with each other by turbulence generated by the second blocks 170b when flowing in the mixing recess 130. Accordingly, the fluid mixing structure 100 of the present embodiment is adapted to mix the reagent liquid L1 and the sample liquid L2 evenly. That is to say, even when the reagent liquid L1 and the sample liquid L2 have lower flowability because the reagent liquid L1 and the sample liquid L2 have low Reynolds numbers, the reagent liquid L1 and the sample liquid L2 may also flow in the ring-shaped channel which is formed by the mixing recess 130 and the first block 170a, and be mixed evenly by turbulence of the second blocks 170b. However, the implementation is merely used to illustrate advantages of the present application. The present application is not limited to use liquids having low Reynolds numbers as the reagent liquid L1 and the sample liquid L2. After the reagent liquid L1 and the sample liquid L2 are mixed evenly into a mixing liquid which is not illustrated, the mixing liquid then flows out of the mixing recess 130 through the second channel 140.

Figure 4:
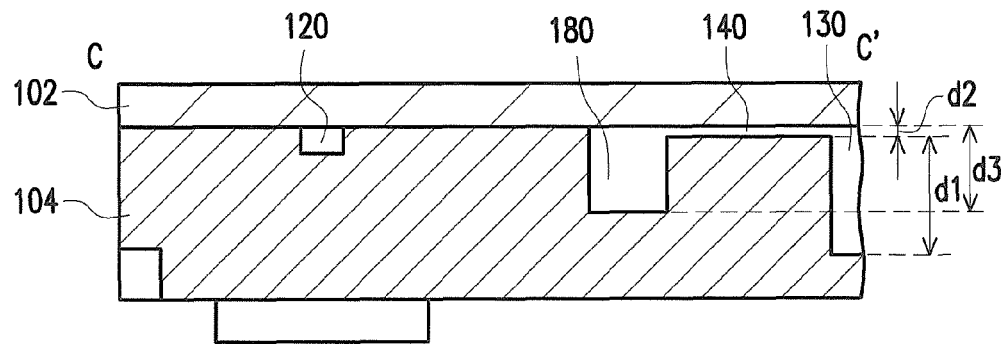
FIG. 4 is a schematic cross-sectional view illustrating the fluid mixing structure depicted in FIG. 1 along line C-C'.

FIG. 4 is a schematic cross-sectional view illustrating the fluid mixing structure depicted in FIG. 1 along line C-C'. With reference to FIG. 1 to FIG. 4, in the present embodiment, the fluid mixing structure 100, as described previously, may be formed by the plates 102 and 104. Thus, the aforesaid channels and recesses may be trenches or recesses which are disposed between the plates 102 and 104. Accordingly, when channels or recesses are located at different level heights due to the trenches or recess have different depths, the reagent liquid and the sample liquid may flow therebetween, or deposition or separation thereof may happen. For example, in the present embodiment, a height hl of the third channel 120 relative to a datum plane (e.g., a bottom surface of the plate 104) is higher than a height h2 of the accommodating recess 110 relative to the datum plane, such that a height drop exists between the third channel 120 and the accommodating recess 110, as shown in FIG. 2 and FIG. 3. Accordingly, the reagent liquid L1 (illustrated in FIG. 3) may flow to the accommodating recess 110 located in a lower position through the third channel 120 located in a higher position. In addition, in the present embodiment, the height h2 of the accommodating recess 110 relative to the datum plane is higher than a height h3 of the first channel 150 relative to the datum plane, such that a height drop exists between the accommodating recess 110 and the first channel 150, as shown in FIG. 2 and FIG. 3. Accordingly, the reagent liquid L1 and the sample liquid L2 (illustrated in FIG. 3) may flow to the first channel 150 located in a lower position from the accommodating recess 110 located in a higher position. Furthermore, in the present embodiment, a depth dl of the mixing recess 130 is deeper than a depth d2 of the second channel 140, i.e., a bottom of the mixing recess 130 is lower than a bottom of the second channel 140, such that a height drop exists between the mixing recess 130 and the second channel 140, as shown in FIG. 4. Accordingly, after the sample liquid and the reagent liquid are mixed into a mixing liquid in the mixing recess 130, partial ingredients of the mixing liquid are separated through deposition in the mixing recess 130, wherein, since the height drop exists between the mixing recess 130 and the second channel 140, the partial ingredients which are separated from the mixing liquid are deposited in the bottom of the mixing recess 130, and the mixing liquid without the separated partial ingredients flows out of the mixing recess 130 through the second channel 140 due to the height drop.

Moreover, the inspecting module further includes a plurality of settling recess 180 and a fourth channel 190. The settling recesses 180 are communicated with the second channel 140 and the fourth channel 190, so that the mixing liquid may flow into the settling recesses 180 from the mixing recess 130 through the second channel 140. Similarly, a depth d3 of the settling recesses 180 is deeper than a depth of the fourth channel 190 (not marked), i.e., a bottom of the settling recesses 180 is lower than a bottom of the fourth channel 190, such that a height drop exists between the settling recesses 180 and the fourth channel 190. Accordingly, after the mixing liquid flows into the settling recesses 180 from the mixing recess 130 through the second channel 140, partial ingredients of the mixing liquid are separated through deposition in the settling recesses 180. In other words, partial ingredients in the mixing liquid from which the partial ingredients are separated in the mixing recess 130 may again be separated through deposition in the settling recesses 180, and the mixing liquid without the separated partial ingredients flows out of the settling recesses 180 from the fourth channel 190 due to the height drop. Thus, it is concluded that different components may be sequentially separated from the mixing liquid through deposition during a flowing process by arranging settling recesses 180 in different quantities and depths. Accordingly, quantities of the settling recess 180 and whether to provide the settling recesses 180 and the fourth channel 190 or not may be adjusted as desired, and the present application is not limited thereto. Afterwards, the partial ingredients which are separated from the mixing liquid through the mixing recess 130 and the settling recesses 180, or the mixing liquid without the separated partial ingredients may be used for inspecting.

With reference to FIG. 1 again, the inspecting module further includes a measurement area R, and the measurement area R is communicated with the second channel 140. Specifically speaking, since the fluid mixing structure 100 of the present embodiment adopts the settling recesses 180 and the fourth channel 190, a substantive implementation of the measurement area R of the present embodiment in communication with the second channel 140 is to allow the fourth channel 190 to pass through the measurement area R. Accordingly, a biochip which is not illustrated is adapted to be disposed in the measurement area R, and the mixing liquid is adapted to flow through the biochip which is located at the measurement area R through the second channel 140, the settling recesses 180 and the fourth channel 190, so that the biochip may inspect biological properties of the mixing liquid which does not contain the separated partial ingredients. More specifically, in the present embodiment, the sample liquid is, for example, blood, and the reagent liquid is, for example, phosphate buffered saline (PBS), but the present application does not limit varieties of the sample liquid and the reagent liquid. Varieties of the reagent liquid may also be correspondingly adjusted based on varieties of the sample liquid and items to be inspected. After the sample liquid and the reagent liquid start biochemical reactions and are mixed into a mixing liquid in the mixing recess 130, the mixing liquid is deposited in the mixing recess 130 and the settling recesses 180 sequentially for partial ingredients (e.g., red blood cells) to be separated therefrom, and then biological properties of the mixing liquid from which partial ingredients are separated are inspected by the biochip which is located at the measurement area R. In addition, in the present embodiment, the biochip located in the measurement area 190 may be electrically connected to an inspection system which is not illustrated herein. When the mixing liquid from which the partial ingredients are separated flows through the biochip, the biochip may inspect the mixing liquid and generate an electrical signal containing a biological property to the inspection system, such that the biological property of the mixing liquid may be acquired through the inspection system.

In other words, since the sample liquid and the reagent liquid of the present embodiment have been completely mixed in the mixing recess 130 before being inspected by the biochip, accuracy of inspecting the biological property of the mixing liquid by the biochip may be improved. Accordingly, the fluid mixing structure 100 of the present embodiment is adapted to mix the reagent liquid and the sample liquid evenly before inspecting the biological property of the mixing liquid by the biochip, so as to acquire a more accurate inspecting result. Furthermore, the inspecting module may further be provided with a waste liquid recess which is not illustrated based on needs. The waste liquid recess is communicated with the fourth channel 190, and the measurement area R is located between the second channel 140 and the waste liquid recess. Namely, the mixing liquid which flows through the fourth channel 190 flows through the measurement area R and then flows into and is collected in the waste liquid recess. Accordingly, the waste liquid recess may be configured for collecting used mixing liquid (after being inspected by the biochip). Therefore, after the used mixing liquid flows into and is collected in the waste liquid recess through the fourth channel 190, the inspecting module which includes the fluid mixing structure 100 may be discarded, and it is not necessary to take out the used mixing liquid. However, the present application does not limit to whether to arrange the waste liquid recess or not, as the arrangement may become an option based on needs.

In summary, in the fluid mixing structure of the present application, the first channel, the mixing recess, and the second channel are communicated with each other, wherein the ring-shaped channel is formed in the mixing recess through the first block, and the second blocks are disposed in the ring-shaped channel. Accordingly, the reagent liquid and the sample liquid are adapted to be mixed into the mixing liquid in the ring-shaped channel of the mixing recess, and the mixing liquid then flows out of the mixing recess through the second channel. In this way, a vortex is generated by the reagent liquid and the sample liquid in the ring-shaped channel of the mixing recess due to turbulence of the second blocks, so as to achieve a function of be mixed evenly in the flowing process. In view of the above, the fluid mixing structure of the present application is adapted to mix the reagent liquid and the sample liquid evenly, and the fluid mixing structure may be applied to the inspecting module which adopts the biochip, so as to acquire a more accurate inspecting result when a biological property of the mixing liquid is subsequently inspected by the biochip.

Although the present application has been disclosed with reference to the aforesaid embodiments, they are not intended to limit the present application. It will be apparent to those skilled in the art that various modifications and variations can be made to the structure of the disclosed embodiments without departing from the scope or spirit of the present application. In view of the foregoing, it is intended that the disclosure cover modifications and variations of the specification provided they fall within the scope of the following claims and their equivalents.

What is claimed is:

1. A fluid mixing structure, adapted to mix a reagent liquid and a sample liquid, the fluid mixing structure comprising:
    a first channel;
    a mixing recess, communicating with the first channel, the reagent liquid and the sample liquid flowing into the mixing recess through the first channel;
    a first block, disposed in the mixing recess, so that the mixing recess becomes a ring-shaped channel by the first block;
    a plurality of second blocks, disposed in the ring-shaped channel, the reagent liquid and the sample liquid being mixed into a mixing liquid in the ring-shaped channel;
    a second channel, communicating with the mixing recess, the mixing liquid flowing out of the mixing recess through the second channel; and
    two plates, bonded together, wherein the mixing recess and the second channel are disposed on the plates and located between the plates after the plates are bonded.

2. The fluid mixing structure as claimed in claim 1, wherein the first block and the second blocks are a cylinder, and diameters of the second blocks are inconsistent.

3. The fluid mixing structure as claimed in claim 2, wherein a diameter of the first block is larger than the diameters of the second blocks.

4. The fluid mixing structure as claimed in claim 2, wherein distances from centers of the second blocks to a center of the first block are inconsistent.

5. The fluid mixing structure as claimed in claim 2, wherein a width of the ring-shaped channel ranges between twice and triple the diameters of the second blocks.

6. The fluid mixing structure as claimed in claim 1, wherein a depth of the mixing recess is deeper than a depth of the second channel.

* * * * *